United States Patent [19]
Davis

[11] Patent Number: 5,848,988
[45] Date of Patent: Dec. 15, 1998

[54] INFUSION DEVICE WITH AUDIBLE DATA OUTPUT

[75] Inventor: David L. Davis, San Diego, Calif.

[73] Assignee: ALARIS Medical Systems, Inc., San Diego, Calif.

[21] Appl. No.: 690,164

[22] Filed: Jul. 26, 1996

[51] Int. Cl.⁶ .................................................. A61M 31/00
[52] U.S. Cl. ................................................................ 604/65
[58] Field of Search .............................. 604/65, 67, 131, 604/151; 128/904; 607/60, 62

[56] References Cited

U.S. PATENT DOCUMENTS

| | | | |
|---|---|---|---|
| 4,337,377 | 6/1982 | Van Riper et al. ................ | 128/904 X |
| 4,373,527 | 2/1983 | Fischell . | |
| 5,074,756 | 12/1991 | Davis .................................... | 604/67 X |
| 5,376,070 | 12/1994 | Purvis et al. ......................... | 604/31 |
| 5,395,320 | 3/1995 | Padda et al. ......................... | 604/65 |
| 5,433,736 | 7/1995 | Nilsson ................................ | 128/904 X |
| 5,506,570 | 4/1996 | Scott et al. .......................... | 340/603 |
| 5,544,649 | 8/1996 | David et al. ........................ | 128/904 X |
| 5,563,584 | 10/1996 | Rader et al. ........................ | 604/67 X |
| 5,573,506 | 11/1996 | Vasko ................................... | 604/51 X |

Primary Examiner—Max Hindenburg
Attorney, Agent, or Firm—Fulwider, Patton & Utecht, LLP

[57] ABSTRACT

A small, portable infusion device for ambulatory use by a patient includes an audible enunciator integrated circuit chip. This chip is controlled by a microprocessor to provide output data to an operator, and to work in place of, or in association with a visual output display, such as an LCD screen. The audible data output permits a remote clinician to monitor operation of the pump, and diagnose and correct problems with the pump's operation.

21 Claims, 3 Drawing Sheets

INFUSION DEVICE WITH AUDIBLE DATA OUTPUT

BACKGROUND OF THE INVENTION

1. General Background

This invention relates generally to a medication infusion device for administering fluid to patients and more particularly to an improved, ambulatory infusion device with a disposable administration set which is inexpensive to manufacture, convenient to operate and which ensures fluid delivery at a consistent and uniform rate. More specifically, this invention relates to an annunciator system for such an ambulatory infusion device which permits status data and the like to be audibilized. In addition to assisting a patient in controlling the infusion device, this feature permits a remote clinician to monitor the status of the device, accurately change infusion profiles and other device parameters, and diagnose alarm indications, all over normal telephone lines, and without special telephone equipment.

2. Description of the Prior Art

As a result of the ongoing need for improved health care, there is a continuous effort to improve the administration of intravenous fluid to patients. As is well known, medication dispensers and infusion devices are used for infusion of predetermined amounts of medication into the body of a patient. Various types of medication dispensers employing different techniques for a variety of applications are known to exist.

In many cases it is of critical importance to provide precisely controlled and consistent flow rates of intravenous fluid to patients. This need for more controlled IV flow rates is only partially fulfilled by prior art pumps. Specifically, when a patient or nurse experiences a problem with a pump, they typically call a 24 hour "hotline" for clinical assistance. The called clinician is well versed on the proper operation of the infusion device and attempts to resolve the issue or reprogram the pump by asking the patient or nurse a variety of questions. For example, the clinician may inquire as to the current programming of the pump, the indicators or alarms that are being or have been displayed on the pump, as well as the status of the infusion. Status information may include, for example, how much medication has already been infused, how much of the current medicine dose has been infused, what has been the mean time between patient activated bolus requests, and the like.

The information relayed by the patient or nurse to the clinician is vital in order to properly determine whether there is a problem, to diagnose the problem if one exists, and to take the necessary corrective actions to remedy the problem or to reprogram the pump. The accuracy of the relayed information is critical, and misinformation could result in some instances, in serious patient injury.

This communication problem is often compounded by the fact that the patient, usually unattended by a clinician, is frequently under the effects of a narcotic, such as morphine, and possibly compromised from pain or other effects of the illness being treated. As a consequence of these or other factors, the patient's interpretation of the indications and program information, typically read from a small LCD display on the pump body, is sometimes incorrect. For example, the patient may fail to see or report a decimal point. Complicating matters further, many patients, especially diabetics, have compromised sight and are unable to read the LCD indications and program from the infusion device.

Even in circumstances where the assistance of a remote clinician is not needed, patients with impaired vision or perception, due to drugs or illness, often have difficulty assuring that they are correctly operating or programming the infusion device, or correctly interpreting alarm indications from the pump.

Existing pumps which use LCD displays to provide status information to the patient require that a compromise be made between pump portability, pump cost, and data clarity or completeness. In order to reduce cost, and to make ambulatory pumps as small and lightweight as possible, manufacturers must reduce the size of visual displays, such as LCD displays, as much as possible. Small displays, however, are difficult for patients to read, and will provide only two or three word outputs at any one time, compromising instruction or status understandability.

SUMMARY OF THE INVENTION

The present invention provides an improvement which supplements or completely replaces the visual output, such as the LCD output, on an ambulatory infusion device or pump. An integrated circuit chip capable of storing recorded words is included within the infusion device. This chip stores a vocabulary which is specifically selected for this infusion device, and includes, for example, verbalizations of alarms, numbers, control function names, etc. This chip is controlled by the microprocessor which operates the pump, and each of the stored words or phrases is individually addressable by the microprocessor. Thus, the microprocessor can form strings of words or phrases together by addressing, in succession, words or phrases from the vocabulary. In this way, the microprocessor, in response to measured pump parameters or the depression of control keys on the pump, can create phrases or sentences which indicate an alarm condition, provide infusion profile data, and explain pump conditions or the like.

Because the output of data is audible, the patient, attending nurse or other helper can hold the ambulatory infusion device near a telephone and dial a remote clinician. The clinician, with the help of the patient or nurse, can direct control keys to be depressed and listen, over the telephone, to the pump's audible response.

In essence, the present invention permits the remote clinician to bypass the patient's interpretation of the condition of the pump and to get the information directly and accurately from the pump itself. Because the voice tone and inflection of the recorded words are easy to recognize, the remote clinician can easily distinguish between words spoken by the patient and words "spoken" by the pump. The remote clinician merely directs the patient to push the appropriate button or key sequence on the pump. The pump then "speaks" its program and infusion status through a transducer, such as a speaker, on the pump directly into the handset of the telephone, without any electrical connection to the telephone. The remote clinician can then hear all the information that is normally available through the displays and indicators on the pump without concern about the accuracy of the information received.

When a problem has been diagnosed by the remote clinician, a reprogramming of the pump is frequently required. The clinician directs the patient or the patient's helper to push the proper button sequence. During this operation, the clinician can verify that the correct button sequence has been pushed by listening as the pump itself audibilizes the name of each depressed key. If the clinician detects a sequence error, they can immediately direct corrective action. After the pump has been reprogrammed in this manner, the clinician can again direct the patient to press the proper button sequence which directs the pump to "speak" its infusion profile and status. This verifies that the reprogramming was successful.

The invention also permits the pump to provide information about its status or the program, which is not normally, or cannot be displayed, on the visual display because of the necessarily small size of the pump and its display. In other words, this speech function can be used to provide information which would not normally justify an increased size or complexity of a visual display.

Another purpose of the invention is to provide audible direction to a programmer or user of the pump on site. This function is comparable to a "help" screen on a computer. An incomplete or incorrect button entry might lead to a verbal direction to appropriately complete the programming (i.e. "push run/stop to resume the infusion" or "push SET to enter the value"). This can be done without a resulting increase in size or cost of the pump.

In some circumstances, the invention can completely replace the visual display on the pump, significantly reducing the cost and size of the pump.

BRIEF DESCRIPTION OF THE DRAWINGS

The preferred embodiment of the present invention is illustrated in and by the following drawings in which like reference numerals indicate like parts and in which.

DETAILED DESCRIPTION OF A PREFERRED EMBODIMENT

Figure 1:
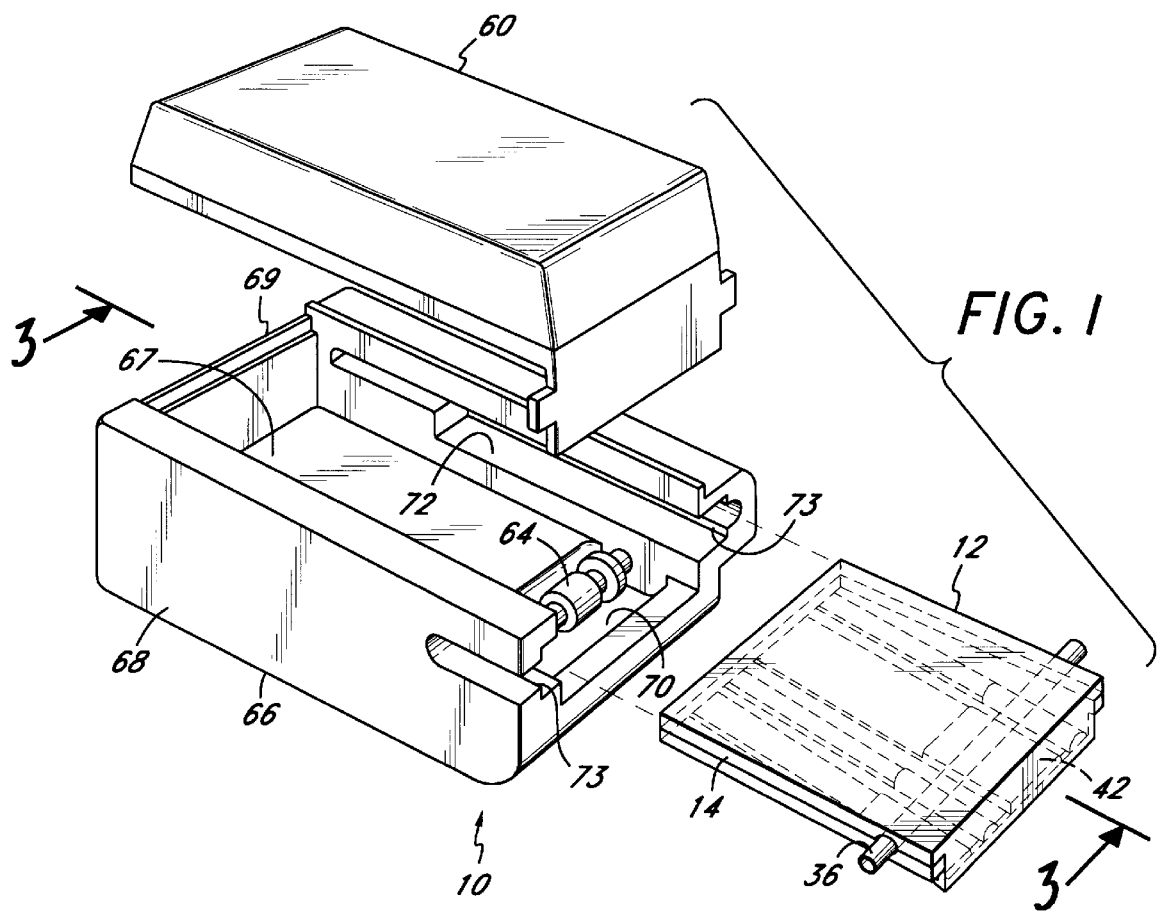
FIG. 1 is a perspective, exploded view illustrating an infusion device having a disposable administration set and an audible data output in accordance with the present invention.
Figure 2:
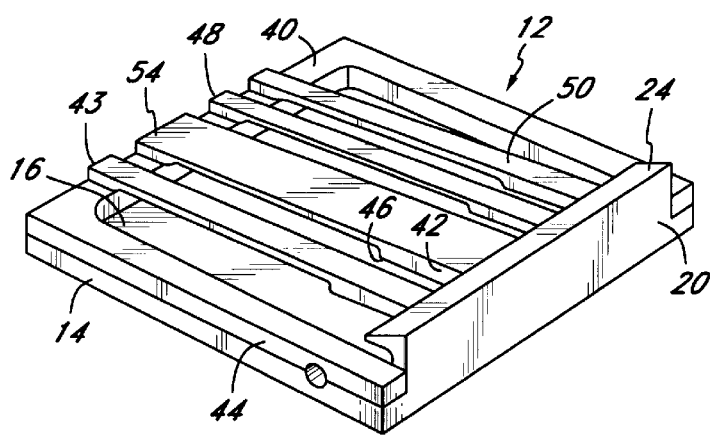
FIG. 2 is a perspective view illustrating a disposable administration set for use with the infusion device of FIG. 1.
Figure 3:
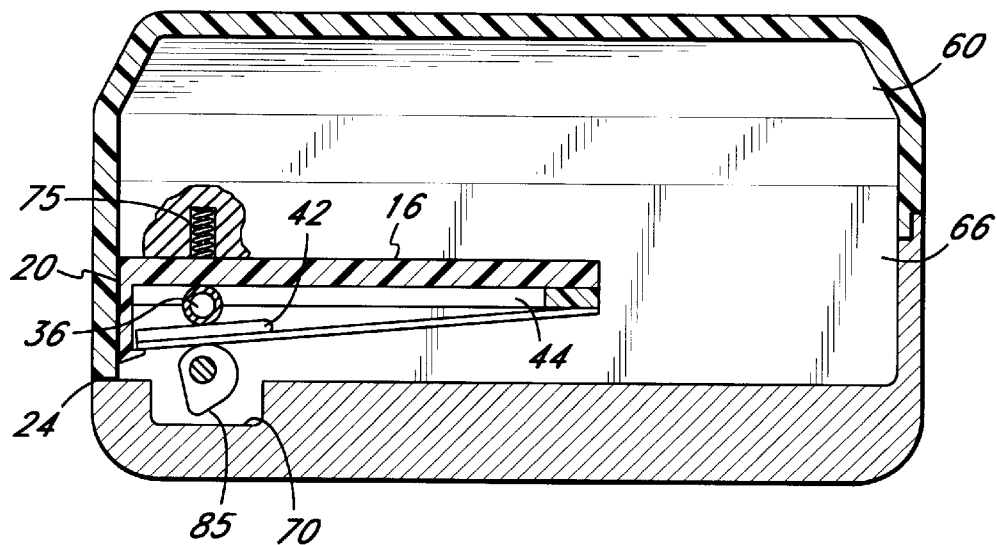
FIG. 3 is a cross section view taken along the line 3—3 of FIG. 1.

FIG. 1 illustrates the infusion device 10 of the present invention for administering intravenous fluid at a consistent and uniform rate. The infusion device 10 is designed to be small, lightweight and ambulatory. The infusion device 10 includes a disposable administration set 12 having a plurality of cam followers 42 which are displaced in a predetermined sequence when depressed by a pumping mechanism 64 to squeeze a delivery tube 36 for dispensing fluid. In FIGS. 1, 2 and 3, an administration set 12 is shown, and will be used to explain the operation of the device 10 by way of background.

The pumping mechanism 64 is driven by a commercially available motor 11 (not shown). The disposable administration set 12 loads easily into the housing structure 66 adjacent the pumping mechanism 64. Oriented directly above the housing structure 66 is an optional fluid reservoir 60 which provides a continuous flow of fluid to the inlet of the delivery tube 36 for dispensing and infusing fluid into a patient's body. Alternatively, the fluid delivery tube 36 may connect to an external reservoir (not shown), or the reservoir 60 may be located at other positions on the assembly.

The housing structure 66 comprises a rectangular chamber 67 surrounded by side walls 68 and a rear wall 69. The floor of the rectangular chamber 67 drops into a recess 70 towards the front end. The pumping mechanism 64 is located within the recess 70. Extending throughout the length and parallel to the base of each of the side walls 68 is a narrow channel 72 having a lower shoulder 73. The disposable administration set 12 slides within the channels 72. As best seen in FIG. 3, each of the channels 72 includes a spring-biased ball assembly 75. The disposable administration set 12, while being manually inserted into the channels 72, depresses the spring assemblies 75. After insertion of the set 12, the spring assemblies on either side bias the disposable administration set 12 against the shoulders 73 of the channels 72, holding the disposable administration set 12 accurately in position. In operation, the disposable administration set 12 is manually loaded into the infusion device 10 in a simple sliding operation. As the administration set 12 slides into the infusion device, the cam followers 42 are gradually pushed against the delivery tube 36 by the pumping mechanism 64.

FIGS. 1, 2 and 3 illustrate the disposable administration set 12 of the present invention, which is formed from rigid plastic or the like, and includes a tubing retainer plate assembly 14 which may advantageously be injection molded as a single piece.

The tubing retainer plate assembly 14 includes a tubing retainer plate 16 having a flat tube-contacting surface and a cam follower retainer 20 projecting normal to this surface at one end. The cam follower retainer 20 terminates in a an overhanging latch 24 projecting substantially parallel to the retainer plate 16. The latch 24 serves as a locking mechanism for holding the cam followers 42 in position, adjacent the tube 36 prior to insertion of the administration set 12 into the housing 66. During insertion of the administration set 12 into the channels 72, some of the cam followers 42 are depressed by the pumping mechanism 64. Between pumping cycles of the various cams, the followers return to a standby position against the latch 24.

Referring to FIG. 3, it will be seen that, after insertion of the administration set 12 into the housing 66, the dispensing tube 36 is positioned immediately below the spring-biased retainer 75. The spring-biased retainer 75 holds the administration set accurately in place against the shoulders 73 (as best seen in FIG. 1). The cam followers 42 are pushed against the tube 36 by a plurality of cams 85, one of which is shown in FIG. 3. Pumping is accomplished by squeezing the tube 36. A more complete description of the pump and its operation to provide a constant, continuous flow of medication to a patient, is provided in U.S. Pat. No. 5,074,756, issued Dec. 24, 1991 to the inventor of the present application, which is hereby incorporated herein by reference.

Figure 4:
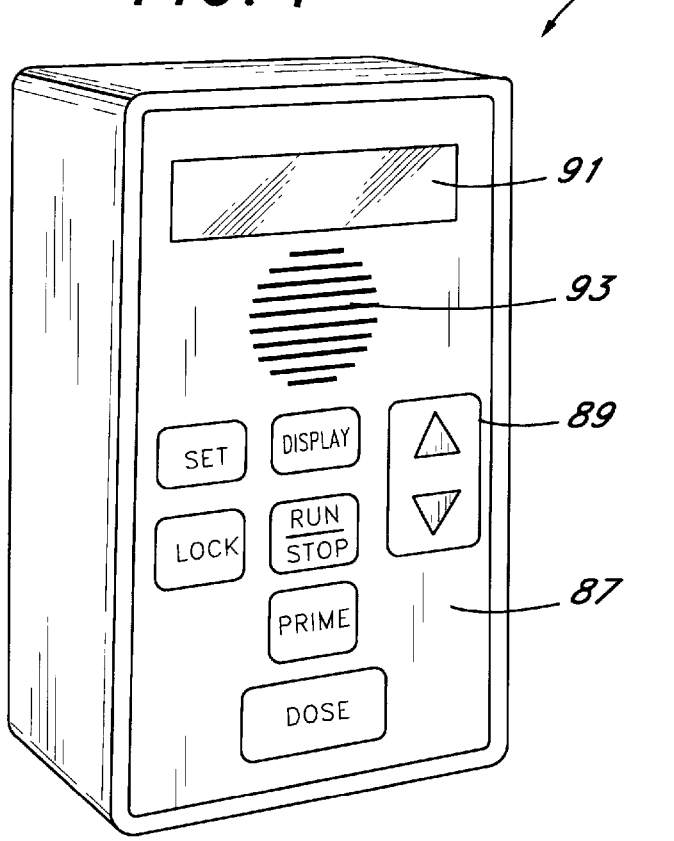
FIG. 4 is a perspective view of the underside of the infusion device of FIG. 1, showing the control buttons or keys, the visual output device and the audible output device.

The underside of the pump 10 (as viewed in FIG. 1) is shown in FIG. 4. This face 87 includes a plurality of keys or buttons 89 for controlling operation of the pump 10, a visual output display 91 which may be, for example, an LCD display, and a speaker grill 93 behind which is mounted a speaker 95 (FIG. 5).

Figure 5:
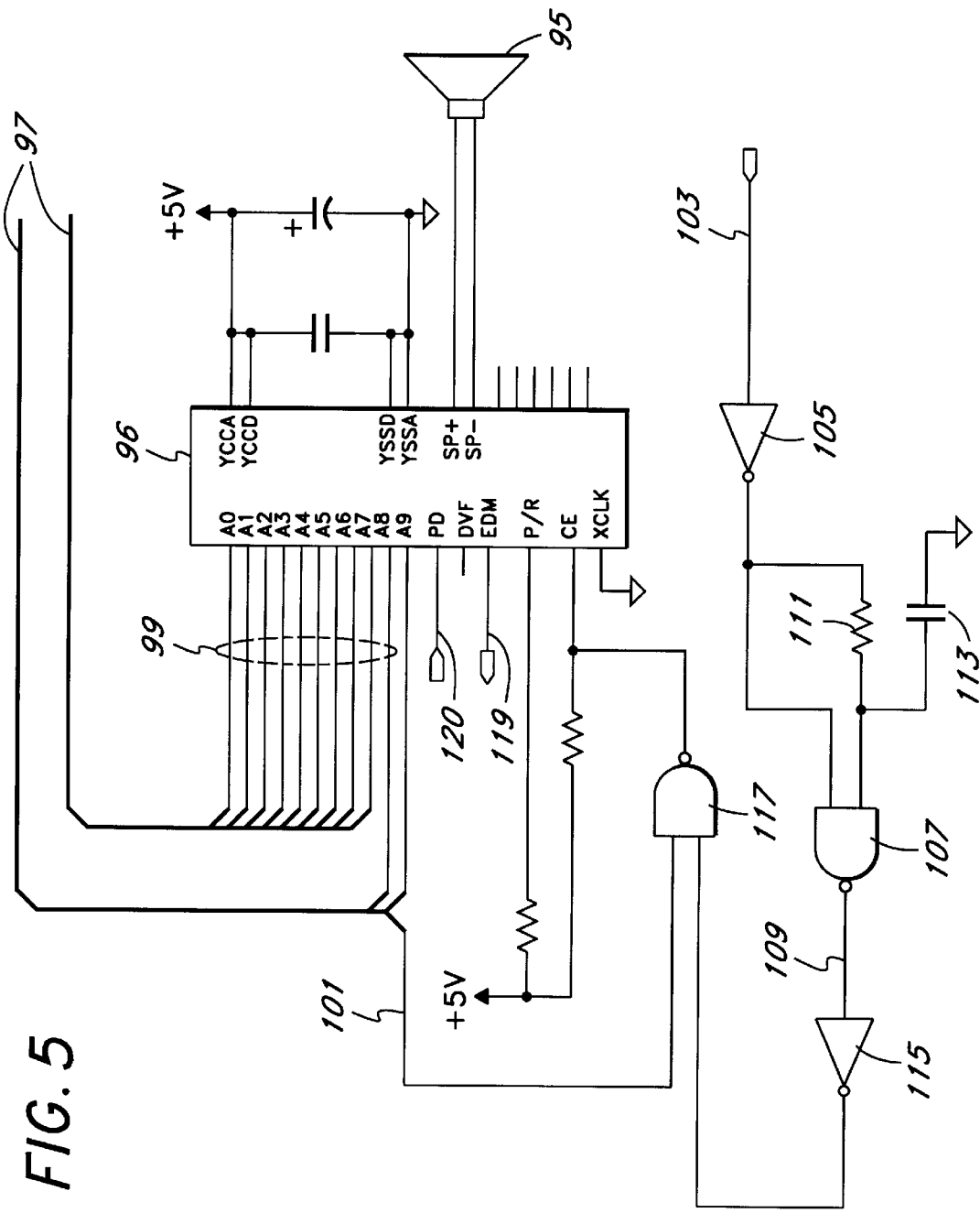
FIG. 5 is a schematic diagram of the audible output chip and its connections to the microprocessor and speaker.

Referring now to FIG. 5, the operation of the vocalizer chip of the present invention will be described. The pump 10 includes a microprocessor (not shown) which operates the pump motor (not shown) to control the drug infusion rate. This microprocessor is controlled, in part, by the buttons or keys 89 shown in FIG. 4, to program pump operation and infusion profiles, to diagnose problems with the pumping mechanism, and the like. Those skilled in the art will recognize that the microprocessor will have other inputs also, which are not unique to the present invention, such as sensors which monitor for occlusions of the tube 36, for air bubbles in the medication, for an empty supply receptacle, or the like.

In addition, the microprocessor is connected to the voice chip circuit 96 of FIG. 5, which is included in the body of the pump 10, by a bus which includes ten address lines 97 and an eleventh address line which is used by the microprocessor to select this device, as opposed to other devices which the microprocessor controls. The ten address lines 97 are used to select specific words from the vocabulary stored in the chip. Once a specific word is addressed, and a microprocessor strobe output on line 103 goes low, the output of an inverter 105 enables a gate 107 to initiate a pulse on line 109. The resistor 111 and capacitor 113 are used to time the trailing edge of this pulse by disabling the gate 107 after a fixed period. The pulse on line 109 is inverted at 115 and, with the select line 101, used to enable a gate 177 which, in turn, causes an addressed word to be "spoken" by the speaker 95. The chip 96 includes an amplifier to enable the chip 96 to directly drive the speaker 95 to vocalize the selected word. In order to conserve battery power, the microprocessor controls input line 120 to power up or power down the chip 96.

At the end of the word, an output signal on line 119 from the chip 96 alerts the microprocessor that a spoken word has ended. This permits the microprocessor to access a different word, and, through a repetition of this process, cause the chip 96 to "speak" phrases and sentences. In the preferred embodiment, the chip 95 is an ISD2500 "Single-Chip Voice Record/Playback Device" manufactured by Information Storage Devices.

While the words and phrases which this system can audibilize is virtually unlimited, examples will be provided with regard to the use of the chip 96 in this invention. First, when the buttons 89 on the infusion pump are depressed, the microprocessor will cause the chip 96 to vocalize the name of the button as, for example, by saying the word "set" or the word "lock." This permits a clinician, over public telephone lines, to confirm that a patient has depressed the right button on the pump.

As a second example, if the pump is in a continuous infusion mode, and the "display" button is depressed, the chip 96 will audibilize current infusion information, by saying, for example, "The dose is XXXX Milliliters, the rate is XXXX milliliters per hour, the bag contains XXXX milliliters." If, on the other hand, the pump is in the continuous infusion mode, and the "display" button is depressed twice in succession, the infusion status is spoken. For example "The elapsed time is XXXX hours and XXXX minutes, XXXX hours and XXXX minutes remain, XXXX Milliliters have been infused, XXXX Milliliters remain to be infused"

The chip 96 is also programmed to audibilize alarm conditions. For example, the pump may respond to a downstream occlusion by the microprocessor causing the chip 96 to audibilize "Downstream occlusion."

In addition, the chip 96 is operated by the microprocessor to provide "help" information. For example, if an incomplete entry is made while the pump is being programmed, the microprocessor may cause the chip 96 to audibilize "push SET to enter the value."

From these examples, it can be seen that the variety of data which can be audibly provided by the invention is almost unlimited. In each instance, the invention provides an audible output, so that a patient can be sure of the button that has been pushed, or the condition of the pump. Of equal importance, the invention provides information to a clinician remote from the patient to enable diagnosis of pump malfunctions, reprogramming of the pump, and assistance to the patient in operating the pump. All of this can be done over the public telephone system, using the standard handset of a standard telephone to receive the messages from the pump, without special adapters such as modems or the like.

In addition to the ability to provide a simple and reliable communication link directly from the pump to a remote clinician, this invention permits this communication without risking shock to the patient, as would occur if the pump were directly wired to a communication network.

Although this invention is described in terms of certain preferred embodiments, other embodiments that are apparent to those of ordinary skill in the art are also within the scope of this invention. Accordingly, the scope of the invention is intended to be defined only by the claims which follow.

I claim:

1. A portable, ambulatory infusion pump, comprising:
   a pump;
   a voice storage device;
   a control circuit connected to activate said voice storage device to output a stored voice signal identifying a parameter of said pump, and
   a transducer mounted on said pump and connected to receive said stored voice signal from said voice storage device to audibilize said stored voice signal.

2. A portable ambulatory infusion pump, as defined in claim 1, wherein said voice storage device comprises a digital voice storage chip which stores a vocabulary of individually addressable words.

3. A portable ambulatory infusion pump, as defined in claim 1, wherein said voice storage device comprises a microprocessor-controlled integrated circuit.

4. A portable ambulatory infusion pump, as defined in claim 1, wherein said control circuit comprises a microprocessor.

5. A portable ambulatory infusion pump, as defined in claim 4, wherein said microprocessor is controlled by keys on said ambulatory infusion pump to access words from said voice storage device.

6. A method of assisting a patient in operating a portable infusion apparatus, comprising:
   receiving plural different patient control inputs into said portable infusion pump;
   producing plural different audible messages from said infusion apparatus in response to said plural patient control inputs, and
   transmitting said audible messages to a remote location over the telephone, using a standard telephone handset to receive the audible messages from said infusion apparatus directly.

7. A method as defined in claim 6, wherein said audible messages include the infusion status of said infusion apparatus.

8. A method as defined in claim 6, wherein said audible messages include an identification of said patient control inputs.

9. A method as defined in claim 6 wherein said audible messages provide the sole data output from said infusion apparatus.

10. A method of assisting a patient in operating a portable infusion apparatus comprising:
    producing audible messages from said infusion apparatus in response to patient control inputs, wherein said audible messages include an identification of said patient control inputs and said patient control inputs include key stroke inputs, and transmitting said audible messages to a remote location over the telephone, using a standard telephone handset to receive the audible messages from said infusion apparatus directly.

11. A method of assisting a patient in operating a portable infusion apparatus, comprising:

producing audible messages from said infusion apparatus in response to patient control inputs, wherein said audible messages include phrases, and transmitting said audible messages to a remote location over the telephone, using a standard telephone handset to receive the audible messages from said infusion apparatus directly.

12. An ambulatory infusion pump, comprising:

a motor for pumping fluid from a reservoir;

a battery for powering said motor;

a speaker mounted on said pump, and a circuit for driving said speaker to audibilize words which indicate parameters of said pump.

13. An ambulatory infusion pump, as defined in claim 12, wherein said circuit is powered by said battery.

14. An ambulatory infusion pump, as defined in claim 12, wherein said circuit comprises a digital voice storage circuit.

15. An ambulatory infusion pump, as defined in claim 12, additionally comprising:

a visual display screen on said pump.

16. An ambulatory infusion pump, as defined in claim 12, wherein said circuit comprises a microprocessor.

17. A method of operating an ambulatory infusion pump having a body, comprising:

providing directions from a location remote from said pump over a telephone, to permit a pump operator to activate control functions on said pump, and providing over said telephone, directly from the body of said pump, audible verbal communication indicating the condition of said pump.

18. A method of operating an ambulatory infusion pump, as defined in claim 17, wherein said condition of said pump is an infusion profile.

19. A method of operating an ambulatory infusion pump, as defined in claim 17, wherein said condition of said pump is an infusion status.

20. A method of operating an ambulatory infusion pump, as defined in claim 17, wherein said condition of said pump is the activation of said control functions.

21. An ambulatory infusion pump, comprising:

a pump body, small enough and light enough to be conveniently worn on a patient's body, an infusion conduit connected to said pump body for supplying medication from said pump to a patient, and a speaker mounted on said pump body, said speaker providing an audible word message source for pump status information.

\* \* \* \* \*